United States Patent

Tahara

(10) Patent No.: US 9,638,622 B2
(45) Date of Patent: May 2, 2017

(54) PARTICLE DETECTION APPARATUS AND PARTICLE DETECTION METHOD

(71) Applicant: SONY CORPORATION, Tokyo (JP)

(72) Inventor: Katsutoshi Tahara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/652,433

(22) PCT Filed: Oct. 15, 2013

(86) PCT No.: PCT/JP2013/077883
§ 371 (c)(1),
(2) Date: Jun. 15, 2015

(87) PCT Pub. No.: WO2014/097724
PCT Pub. Date: Jun. 26, 2014

(65) Prior Publication Data
US 2015/0338335 A1 Nov. 26, 2015

(30) Foreign Application Priority Data
Dec. 21, 2012 (JP) ................... 2012-278881

(51) Int. Cl.
*G01N 15/14* (2006.01)
*G01N 21/49* (2006.01)
(Continued)

(52) U.S. Cl.
CPC ..... *G01N 15/1429* (2013.01); *G01N 15/1434* (2013.01); *G01N 15/1459* (2013.01);
(Continued)

(58) Field of Classification Search
CPC ........... G01N 15/1429; G01N 15/1434; G01N 21/49; G01N 15/1484; G01N 15/1459; G01N 2015/0053; G01N 2015/1006
(Continued)

(56) References Cited

U.S. PATENT DOCUMENTS 4,906,094 A * 3/1990 Ashida ............... G01N 15/0205
356/246
5,125,737 A * 6/1992 Rodriguez ......... G01N 15/1459
356/338

(Continued)

FOREIGN PATENT DOCUMENTS

JP    HEI 10-019885 A    1/1998
JP    2002-031594 A    1/2002
(Continued)

*Primary Examiner* — Sang Nguyen
(74) *Attorney, Agent, or Firm* — Chip Law Group

(57) ABSTRACT

A particle detection apparatus and a particle detection method capable of accurately detecting scattered light are provided. A scattered light detection unit of the particle detection apparatus having at least a light illumination unit for illuminating a particle with light and the scattered light detection unit for detecting scattered light emitted from the particle illuminated with light is provided with a first detection portion for detecting scattered light, a second detection portion for detecting illumination light onto a particle, and a signal processing unit for removing a noise component from a signal detected in the first detection portion based on a signal detected in the second detection portion.

16 Claims, 8 Drawing Sheets

(51) Int. Cl.
*G01N 15/00* (2006.01)
*G01N 15/10* (2006.01)

(52) U.S. Cl.
CPC ......... *G01N 15/1484* (2013.01); *G01N 21/49* (2013.01); *G01N 2015/0053* (2013.01); *G01N 2015/1006* (2013.01)

(58) Field of Classification Search
USPC ...... 356/335–343, 72–73, 28, 39; 422/82.09, 422/82.05, 82.08
See application file for complete search history.

(56) References Cited

U.S. PATENT DOCUMENTS

| | | | | |
|---|---|---|---|---|
| 5,133,602 A | * | 7/1992 | Batchelder | G01N 15/0205 356/364 |
| 5,185,641 A | * | 2/1993 | Igushi | G01N 15/0211 356/336 |
| 5,416,580 A | * | 5/1995 | Trainer | G01N 15/0211 356/336 |
| 5,492,833 A | * | 2/1996 | Rodriguez | G01N 15/12 356/39 |
| 5,561,515 A | * | 10/1996 | Hairston | G01P 5/26 356/28 |
| 5,898,487 A | * | 4/1999 | Hage | G01N 21/532 356/39 |
| 6,778,271 B2 | * | 8/2004 | Watson | G01N 15/0211 356/336 |
| 7,430,046 B2 | * | 9/2008 | Jiang | G01N 15/0205 356/336 |
| 7,554,663 B2 | * | 6/2009 | Hairston | G01J 3/02 250/458.1 |
| 2007/0146703 A1 | * | 6/2007 | Adams | G01N 15/147 356/337 |
| 2012/0287435 A1 | * | 11/2012 | Adams | G01N 21/51 356/340 |
| 2014/0087453 A1 | * | 3/2014 | Tahara | G01N 15/1434 435/288.7 |

FOREIGN PATENT DOCUMENTS

| | | |
|---|---|---|
| JP | 2002-243624 A | 8/2002 |
| JP | 2005-055233 A | 3/2005 |
| JP | 2012-026837 A | 2/2012 |
| JP | 2012-073070 A | 4/2012 |

\* cited by examiner

PARTICLE DETECTION APPARATUS AND PARTICLE DETECTION METHOD

TECHNICAL FIELD

The present disclosure relates to a particle detection apparatus and a particle detection method for optically detecting particles. More particularly, it relates to a technology for detecting light scattered from a particle illuminated with light.

BACKGROUND ART

An optical detection method using flow cytometry (flow cytometer) is used for identifying biological microparticles such as cells, microorganisms, and liposomes. Flow cytometry is an analysis method of identifying a plurality of particles one by one by illuminating particles flowing in a line through a flow path with laser light of a predetermined wavelength, and detecting fluorescence or scattered light emitted from each particle.

When target particles are cells, for example, by detecting forward scattered light (forward scatter: FS), information on the shape, size, surface state, formation of or presence or absence of a nucleus, or the like can be acquired. Forward scattered light from a target particle is generally detected by a light detector such as a photodiode, where light other than forward scattered light such as illumination light (hereinafter, also referred to as zero-order light) also enters.

As a technology for reducing the effect of light other than target scattered light, for example, there is a light scattering type particle detector having a light-receiving means formed with a plurality of photoelectric elements, and provided with an addition processing means for adding outputs of these photoelectric elements (see Patent Document 1). There is also a technology for removing unnecessary light by disposing a light-shielding mask on the optical path of scattered light. In addition, a microparticle measurement apparatus in which an optical filter is disposed in place of a light-shielding mask to improve the efficiency of detecting scattered light has also been proposed (see Patent Document 2).

CITATION LIST

Patent Document

Patent Document 1: JP 2002-31594 A
Patent Document 2: JP 2012-26837 A

SUMMARY OF THE INVENTION

Problems to be Solved by the Invention

However, the technology described in Patent Document 1 tries to improve the S/N ratio, the ratio between the signal amount and the noise amount, by increasing the light-receiving amount of scattered light, and cannot provide a sufficient effect when a light component other than forward scattered light is great. By contrast, by using an optical filter or a light-shielding mask as in the apparatus described in Patent Document 2, a light component other than forward scattered light can be reduced, but the light component other than the forward scattered light cannot be completely intercepted because of its structure.

The light component other than the forward scattered light (leakage light) that cannot be intercepted by the optical filter directly enters the light detector, and thus causing degradation in the S/N ratio of detected signals. In particular, as the size of detection target particles becomes smaller, the signal level of forward scattered light becomes smaller, thus further increasing the effect of leakage light.

Thus, the present disclosure has a main object of providing a particle detection apparatus and a particle detection method capable of accurately detecting scattered light.

Solutions to Problems

A particle detection apparatus according to the present disclosure includes: a light illumination unit for illuminating a particle with light; and a scattered light detection unit for detecting scattered light emitted from the particle illuminated with light, the scattered light detection unit including: a first detection portion for detecting the scattered light; a second detection portion for detecting a light component originating in the illumination light onto the particle; and a signal processing unit for removing a noise component from a signal detected in the first detection portion based on a signal detected in the second detection portion.

In the particle detection apparatus, the first detection portion and the second detection portion may be provided in a single light detector.

In that case, the first detection portion can be provided around the second detection portion.

Further, the light detector may have a light-receiving surface divided into nine or more areas.

In addition, an illumination light removing member can be disposed in front of the light detector, the illumination light removing member intercepting the light component originating in the illumination light.

On the other hand, the particle detection apparatus may further include a scattered light detector functioning as the first detection portion, and an illumination light detector functioning as the second detection portion.

In that case, the illumination light detector and the scattered light detector can be disposed in this order on the optical path of the scattered light.

Further, an illumination light removing member may be disposed between the illumination light detector and the scattered light detector, the illumination light removing member intercepting the light component originating in the illumination light.

Alternatively, the particle detection apparatus can further include a mirror for changing the optical path of the light component originating in the illumination light, and the illumination light detector can be disposed outside the optical path of the scattered light.

In that case, an illumination light removing member can be disposed between the mirror and the scattered light detector, the illumination light removing member intercepting the light component originating in the illumination light.

The signal processing unit may remove the noise component by subtracting a detection signal of the second detection portion multiplied by a gain value from a detection signal of the first detection portion.

Further, the scattered light is forward scattered light, for example.

In addition, the light illumination unit may illuminate a particle flowing through a flow path with light, and the flow path may be formed in a microchip.

A particle detection method according to the present disclosure includes: a light illumination step of illuminating a particle with light; a scattered light detection step of detecting scattered light emitted from the particle in a first detection portion; an illumination light step of detecting a light component originating in the illumination light onto the particle in a second detection portion; and a signal processing step of removing a noise component from a signal detected in the first detection portion based on a signal detected in the second detection portion.

In the signal processing step, the noise component may be removed by subtracting the detection signal of the second detection portion multiplied by a gain value from the detection signal of the first detection portion.

Further, the gain value can be set based on the detection signal in the first detection portion and the detection signal in the second detection portion when light is emitted in the absence of the particle.

Effects of the Invention

According to the present disclosure, a noise component is removed from a scattered light detection signal, and thus scattered light can be accurately detected.

BRIEF DESCRIPTION OF DRAWINGS

FIG. 3A is a graph showing a signal detected in a scattered light detection area 41a.

FIG. 3B is a graph showing a signal detected in a zero-order light detection area 41b.

MODE FOR CARRYING OUT THE INVENTION

Hereinafter, modes for carrying out the present disclosure will be described in detail with reference to the accompanying drawings. The present disclosure is not limited to embodiments described below. The description will be provided in the following order.

1. First Embodiment
(An Example of a Particle Detection Apparatus in which a Light Detector is Provided with Two Types of Detection Area)
2. Modification Example of First Embodiment
(An Example of a Particle Detection Apparatus in which a Zero-Order Light Removing Member is Disposed in Front of a Light Detector)
3. Second Embodiment
(An Example of a Particle Detection Apparatus with Two Types of Light Detector)
4. First Modification Example of Second Embodiment
(An Example of a Particle Detection Apparatus with a Zero-Order Light Detector and a Zero-Order Light Removing Member)
5. Second Modification Example of Second Embodiment
(An Example of a Particle Detection Apparatus in which a Zero-Order Light Detector is Provided Outside the Optical Path of Scattered Light)

<1. First Embodiment>
[Entire Configuration of Apparatus]

Figure 1:
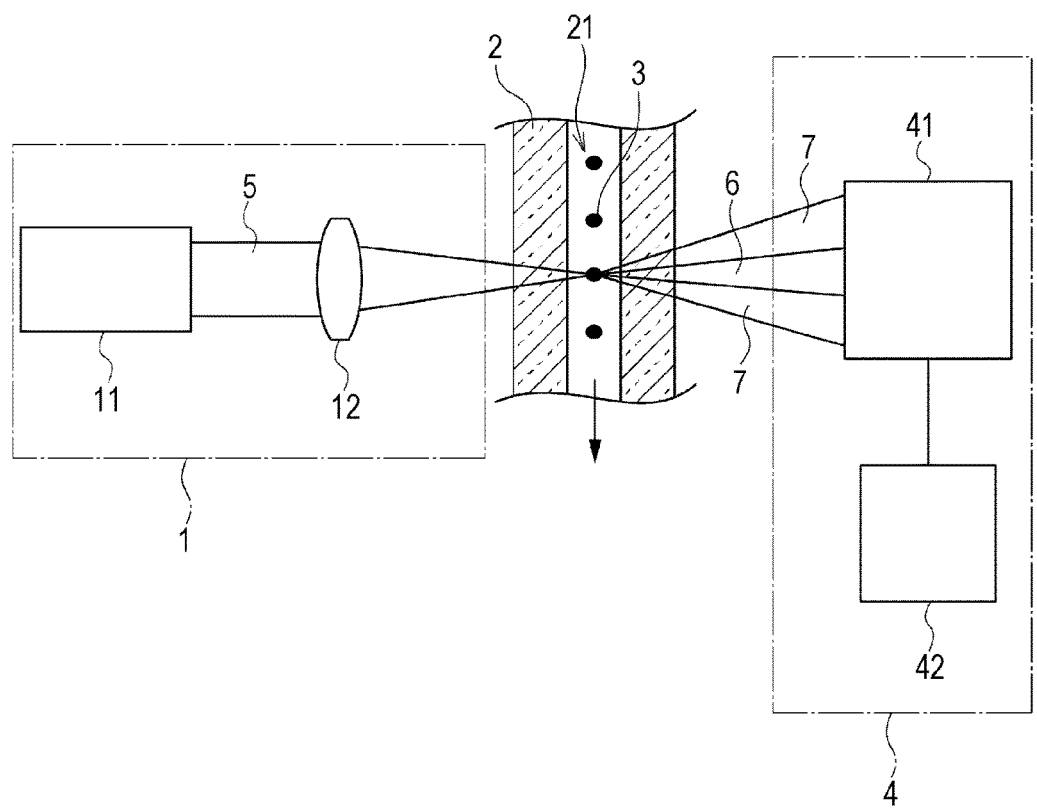
FIG. 1 is a diagram schematically illustrating a configuration of a particle detection apparatus in a first embodiment of the present disclosure.

First, a particle detection apparatus in a first embodiment of the present disclosure will be described with a case where microparticles flowing through a flow path are detected as an example. FIG. 1 is a diagram schematically illustrating a configuration of the particle detection apparatus in this embodiment. As illustrated in FIG. 1, the particle detection apparatus in this embodiment includes a light illumination unit 1 for illuminating a microparticle 3 with light, and a scattered light detection unit 4 for detecting scattered light 7 emitted from the microparticle 3 illuminated with light.

[Light Illumination Unit 1]

The light illumination unit 1 is provided with a light source 11 for generating excitation light 5 such as laser light, a lens 12 for concentrating the excitation light 5 generated by the light source 11 onto the microparticle 3, and others. The light illumination unit 1 illuminates the microparticle 3 flowing through a flow path 21 formed in a microchip 2, for example, with the excitation light 5.

[Microchip 2]

The microchip 2 is provided with the flow path 21 through which the microparticles 3 can flow. A sample liquid containing the detection target microparticles 3, for example, is introduced into the flow path 21. The microchip 2 can be formed with glass or various types of plastic (such as PP, PC, COP, and PDMS). The material of the microchip 2 is not particularly limited, but is desirably a material having transparency for the excitation light 5 emitted from the light illumination unit 1, and a small optical error.

The microchip 2 can be formed by wet etching or dry etching of a glass substrate, or by a nanoimprinting, injection molding, or machining of a plastic substrate. By sealing a substrate formed with the flow path 21 and others with a substrate of the same material or a different material, the microchip 2 can be formed.

[Microparticle 3]

The "microparticles" 3 detected by the particle detection apparatus in this embodiment include biological microparticles such as cells, microorganisms, and ribosomes, synthetic particles such as latex particles, gel particles, and industrial particles, and others broadly.

Biological microparticles include chromosomes, ribosomes, mitochondrion, organelles (cell organelles), and the like constituting various cells. Cells include plant cells, animal cells, blood cells, and the like. Microorganisms include bacilli such as colon *bacilli*, viruses such as tobacco mosaic viruses, fungi such as yeast fungi, and the like. The biological microparticles can also include biological copolymers such as nucleic acids, proteins, complexes of them, and the like.

Industrial particles include those formed with organic polymeric materials, inorganic materials, metal materials, and the like. As organic polymeric materials, polystyrene, styrene-divinylbenzene, polymethylmethacrylate, and the like can be used. As inorganic materials, glass, silica, magnetic materials, and the like can be used. As metal materials, for example, gold colloids, aluminum, and the like can be used. The shapes of these microparticles are generally spherical, but may be non-spherical. The sizes and weights of them are also not particularly limited.

[Scattered Light Detection Unit 4]

The scattered light detection unit 4 detects the scattered light 7 emitted from the microparticle 3 illuminated with the excitation light 5, and is provided with a light detector 41 and a signal processing unit 42.

(Light Detector 41)

Figure 2:
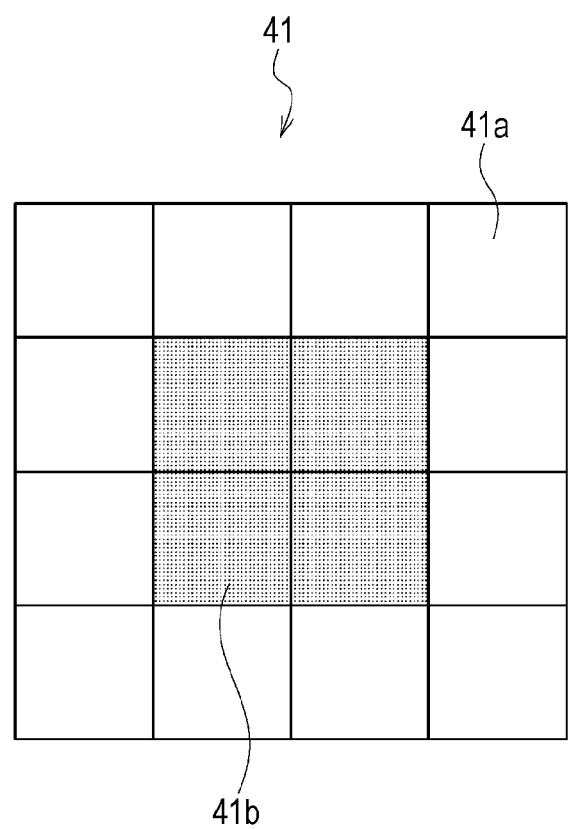
FIG. 2 is a schematic diagram illustrating a detection area of a light detector 41 illustrated in FIG. 1.

The light detector 41 is constituted by a photodiode or the like, and detects the forward scattered light 7 emitted from the microparticle 3 illuminated with light and also a light component (zero-order light 6) other than the forward scattered light 7, such as the excitation light 5. FIG. 2 is a schematic diagram illustrating a detection area of the light detector 41. As illustrated in FIG. 2, alight-receiving surface of the light detector 41 is divided into a zero-order light detection area 41b for detecting the zero-order light 6 and a scattered light detection area 41a for detecting the forward scattered light 7.

The forward scattered light 7 is light scattered at an acute angle (to 19°) with respect to the optical axis of the excitation light 5. Thus, of the light entering the light detector 41, a light component around the optical axis is mainly the zero-order light 6, and does not include the forward scattered light 7. Therefore, the light-receiving surface of the light detector 41 has the zero-order light detection area 41b at a central portion and the scattered light detection area 41a provided around it.

Here, the number of divisions of the light-receiving surface of the light detector 41 is not particularly limited, but, in terms of improvement in differential effects described below, is preferably nine divisions (3×3) or more, and more preferably sixteen divisions (4×4) or more. By increasing the number of divisions of the light-receiving surface of the light detector 41, a noise component can be removed from a signal detected in the scattered light detection area 41a without using a gain value in signal processing by the signal processing unit 42 described below.

(Signal Processing Unit 42)

The signal processing unit 42 removes a noise component from a signal detected in the scattered light detection area 41a, based on a signal detected in the zero-order light detection area 41b. Here, light entering the light detector 41 includes various types of noise such as drive current noise of the light source 11, noise of laser light as the excitation light 5, and noise received in the optical path. These types of noise are different in level but are included in both of the zero-order light (leakage light) 6 and the forward scattered light 7 in the same phase.

Therefore, the particle detection apparatus in this embodiment performs processing shown in Expression 1 described below on signals detected in the areas, for example, and sets a signal obtained as a forward scattered light signal. Again value (Gain) in Mathematical Formula 1 below is a value set based on a detection signal in the scattered light detection area 41a and a detection signal in the zero-order light detection area 41b when the excitation light 5 is emitted without the flow of the microparticles 3.

(Forward scattered light signal)=(Detection signal of scattered light detection area 41a)−(Detection signal of zero-order light detection area 41b)× Gain [Mathematical Formula 1]

The particle detection apparatus in this embodiment may be provided with another scattered light detection unit for detecting side scattered light or a fluorescence detection unit for detecting fluorescence emitted from the microparticle 3 as needed.

[Operation]

Next, the operation of the particle detection apparatus in this embodiment, that is, a method of detecting the microparticle 3 using the particle detection apparatus in this embodiment will be described. In the particle detection apparatus in this embodiment, a sample liquid containing the detection target microparticles 3, for example, is introduced into the flow path 21 provided in the microchip 2. Then, the excitation light 5 emitted from the light source 11 is concentrated by the lens 12 or the like to illuminate the microparticle 3 flowing through the flow path 21 in the microchip 2.

Then, the light detector 41 detects the forward scattered light 7 emitted from the microparticle 3 illuminated with the excitation light 5. At this time, the zero-order light 6 into which the excitation light 5 has leaked also enters the light detector 41 in addition to the forward scattered light 7. Therefore, the particle detection apparatus in this embodiment has the light-receiving surface of the light detector 41 provided with the zero-order light detection area 41b and the scattered light detection area 41a to detect both of them.

Figure 3:
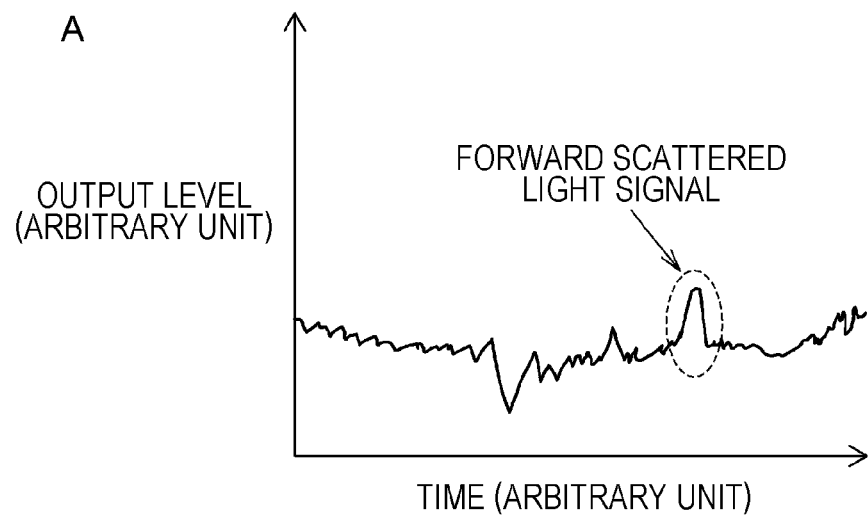
Figure 3:
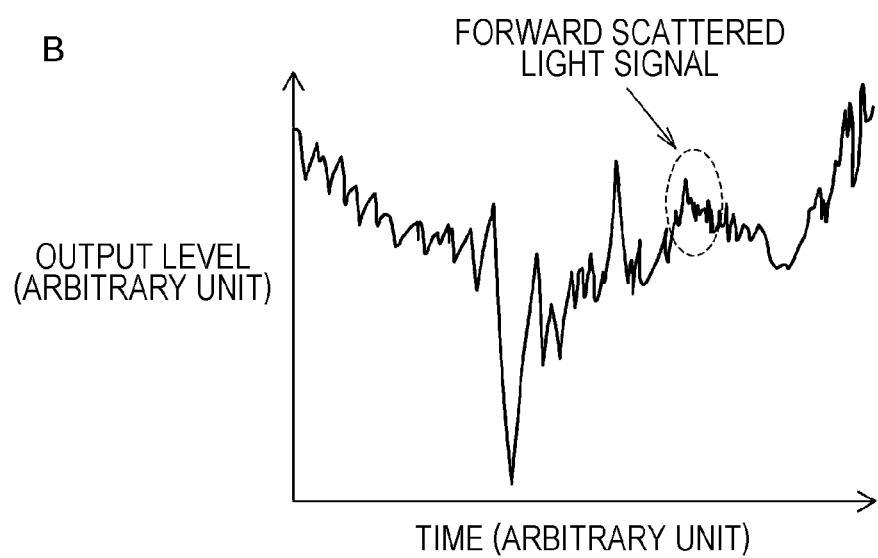

FIG. 3A is a graph showing a signal detected in the scattered light detection area 41a, and FIG. 3B is a graph showing a signal detected in the zero-order light detection area 41b. As illustrated in FIG. 3A, in the scattered light detection area 41a, noise included in the zero-order light 6 and a signal of the forward scattered light 7 are detected. On the other hand, as illustrated in FIG. 3B, in the zero-order light detection area 41b, a signal of the forward scattered light 7 is hardly detected, and a noise component included in the zero-order light 6 is mainly detected.

Here, the noise due to the excitation light 5 detected in the scattered light detection area 41a and the noise included in the zero-order light 6 detected in the zero-order light detection area 41b are different in level but in the same phase. Therefore, in the particle detection apparatus in this embodiment, the signal processing unit 42 removes the noise component from the signal detected in the scattered light detection area 41a, based on the signal detected in the zero-order light detection area 41b.

Figure 4:
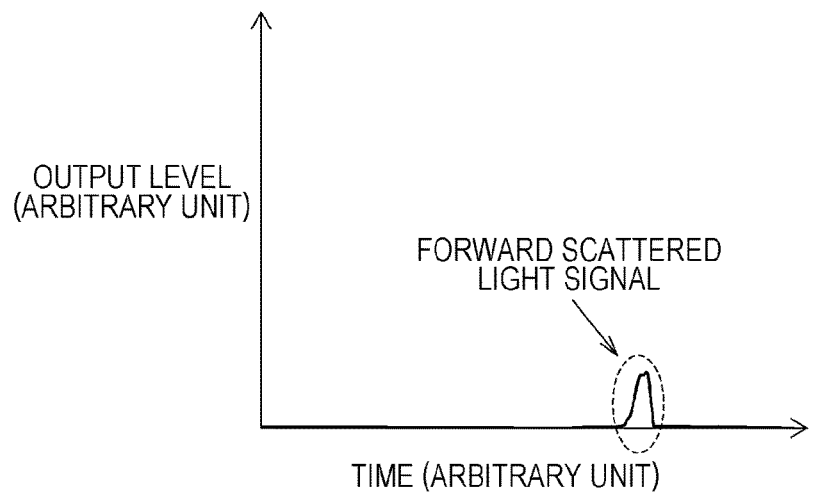
FIG. 4 is a graph showing a signal with a noise component removed by a signal processing unit 42.

Specifically, processing of subtracting a detection signal of the zero-order light detection area 41b multiplied by a gain value from a detection signal of the scattered light detection area 41a shown in Mathematical Formula 1 described above is performed. FIG. 4 is a graph showing a signal with the noise component removed by the signal processing unit 42.

Thus, as illustrated in FIG. 4, only the waveform of a signal almost originating in the forward scattered light 7 is obtained.

Here, the gain value used in the processing performed in the signal processing unit 42 is a value adjusted so that the noise of the forward scattered light 7 and the zero-order light 6 becomes zero. For example, a sample liquid not containing the microparticles 3 is passed through the flow path 21, under which condition a change in the level of noise included in a signal is detected while the gain value is changed, and a value when the noise is eliminated is set as the gain value.

As described in detail above, in the particle detection apparatus in this embodiment, a noise component is removed from a signal detected in the scattered light detection area 41*a*, based on a signal detected in the zero-order light detection area 41*b*, and thus the accuracy of detecting forward scattered light can be improved. Further, in the particle detection apparatus in this embodiment, low-frequency and high-frequency noise included in leakage light (zero-order light 6) entering the scattered light detection area 41*a* can be removed, and thus even when the forward scattered light 7 from the microparticle 3 is minute, it can be detected. This improves the ability of detecting scattered light, and allows implementation of the detection of only an ideal scattered light signal.

In techniques of detecting scattered light of microparticles flowing through a flow path such as a flow cytometer, it is difficult to differentiate between zero-order light and scattered light. However, by applying the present disclosure, these can be separated to accurately detect forward scattered light. The present disclosure is not limited to the case of detecting the microparticles 3 using the microchip 2, and can be applied to various particle detection apparatuses.

Further, the present disclosure can be applied to detection of other scattered light as well as forward scattered light, and provides a similar effect in that case.

<2. Modification Example of First Embodiment>

Figure 5:
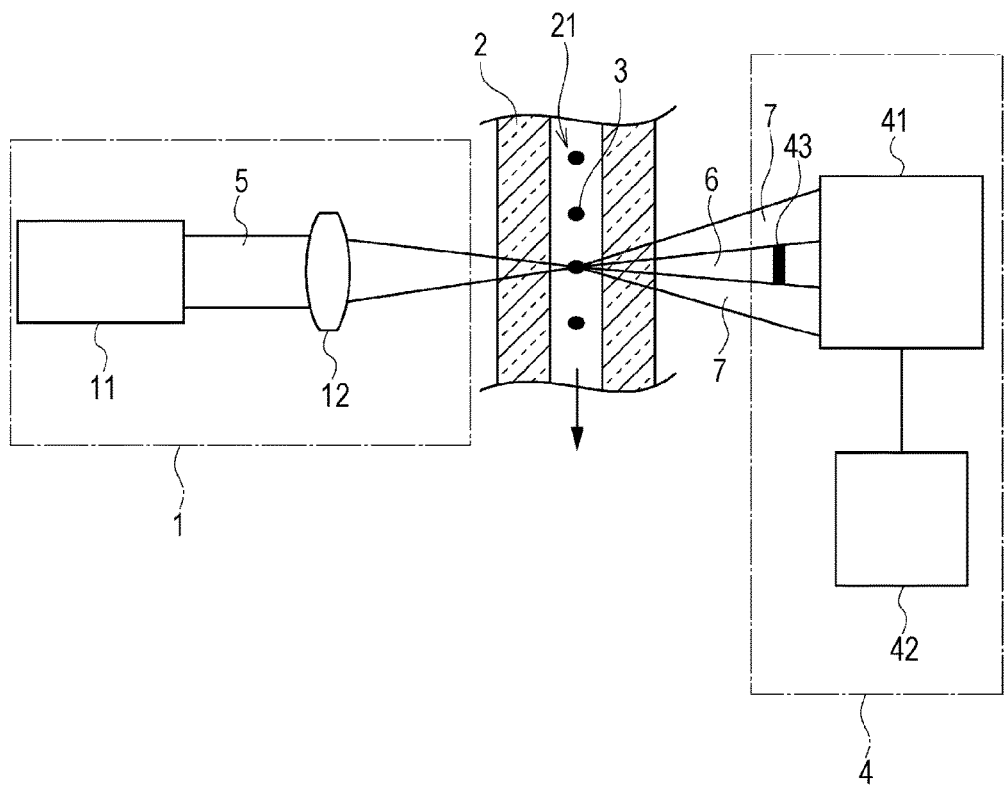
FIG. 5 is a diagram schematically illustrating a configuration of a particle detection apparatus in a modification example of the first embodiment of the present disclosure.
Figure 6:
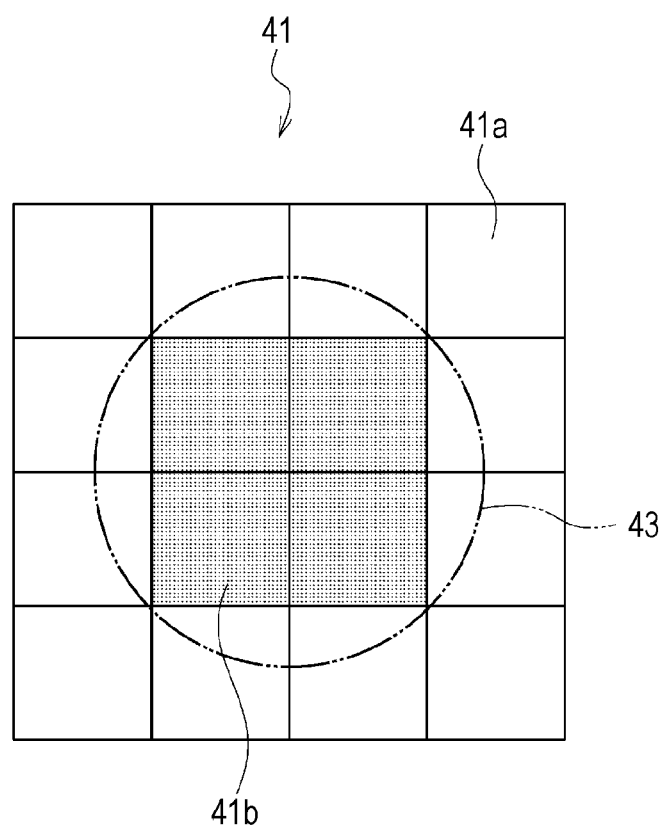
FIG. 6 is a diagram illustrating the positional relationship between the detection area of the light detector 41 and a zero-order light removing member 43 illustrated in FIG. 5.

Next, a particle detection apparatus according to a modification example of the first embodiment of the present disclosure will be described. FIG. 5 is a diagram schematically illustrating a configuration of the particle detection apparatus in this modification example. FIG. 6 is a diagram illustrating the positional relationship between the detection area of the light detector 41 and a zero-order light removing member 43. In FIGS. 5 and 6, the same components as those of the particle detection apparatus in the above-described first embodiment are denoted by the same reference numerals, and will not be described in detail.

As illustrated in FIGS. 5 and 6, in the particle detection apparatus in this modification example, the zero-order light removing member 43 for intercepting the zero-order light 6 is disposed in front of the light detector 41. Here, for the zero-order light removing member 43, a mask, an optical filter for selectively intercepting specific light, or the like can be used, which are not limiting. It may be any optical member capable of intercepting the zero-order light 6.

When the signal intensity of the zero-order light 6 leaking into the scattered light detection area 41*a* is high, it can be difficult to adjust the gain value used in signal processing. However, by disposing the zero-order light removing member 43 as in this modification example, the intensity of the zero-order light 6 can be reduced. Thus, even when the signal intensity of the zero-order light 6 is high, a noise component can be removed to accurately detect forward scattered light.

Components, operation, and effect other than those described above in this modification example are identical to those in the above-described first embodiment.

<3. Second Embodiment>

Figure 7:
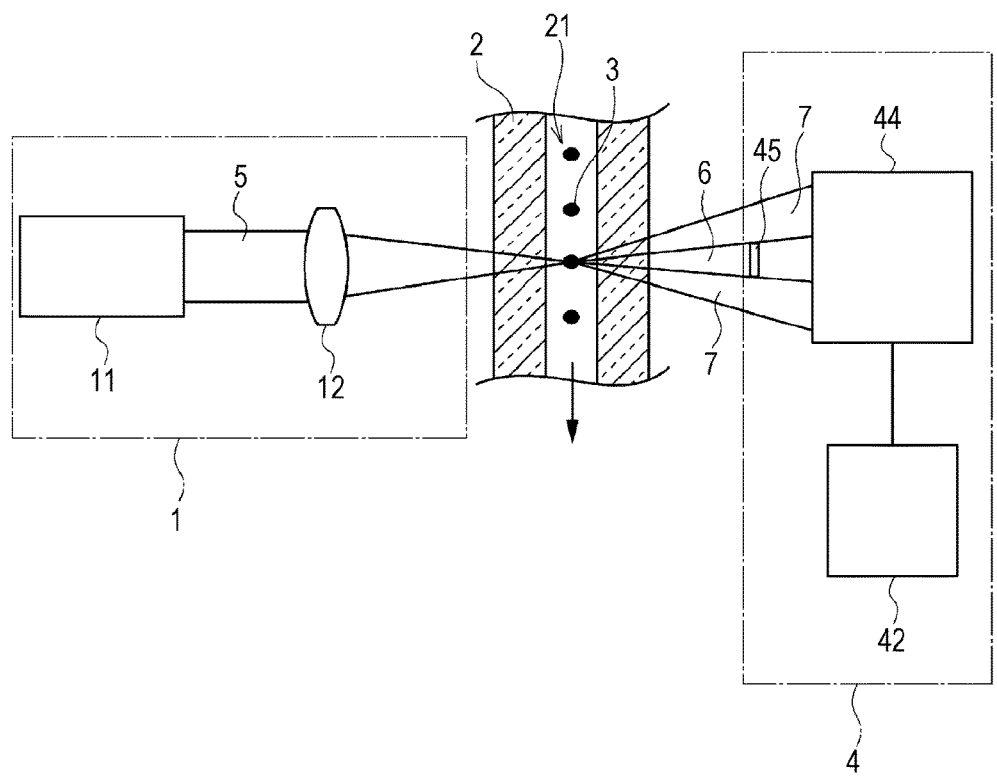
FIG. 7 is a diagram schematically illustrating a configuration of a particle detection apparatus in a second embodiment of the present disclosure.
Figure 8:
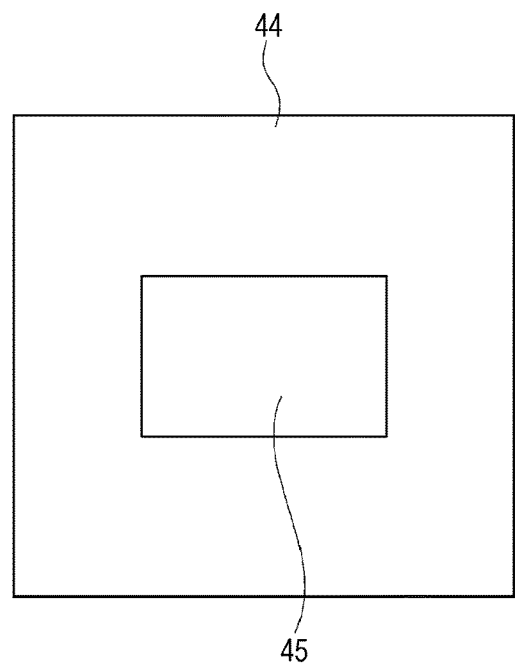
FIG. 8 is a diagram illustrating the positional relationship between a detection area of a scattered light detector 44 and a zero-order light detector 45 illustrated in FIG. 7.

Next, a particle detection apparatus according to a second embodiment of the present disclosure will be described. FIG. 7 is a diagram schematically illustrating a configuration of the particle detection apparatus in this embodiment. FIG. 8 is a diagram illustrating the positional relationship between a detection area of a scattered light detector 44 and a zero-order light detector 45. In FIGS. 7 and 8, the same components as those of the particle detection apparatus in the above-described first embodiment are denoted by the same reference numerals, and will not be described in detail.

As illustrated in FIGS. 7 and 8, in the particle detection apparatus in this embodiment, the zero-order light detector 45 for detecting zero-order light 6 and the scattered light detector 44 for detecting scattered light 7 are disposed in this order on an optical path. Here, for the zero-order light detector 45 and the scattered light detector 44, commonly-used light detectors such as photodiodes may be used.

In the particle detection apparatus in this embodiment, a signal processing unit 42 removes a noise component from a signal detected by the scattered light detector 44, based on a signal detected by the zero-order light detector 45. Thus, the accuracy of detecting forward scattered light can be improved as in the above-described first embodiment.

Components, operation, and effect other than those described above in this embodiment are identical to those in the above-described first embodiment.

<4. First Modification Example of Second Embodiment>

Figure 9:
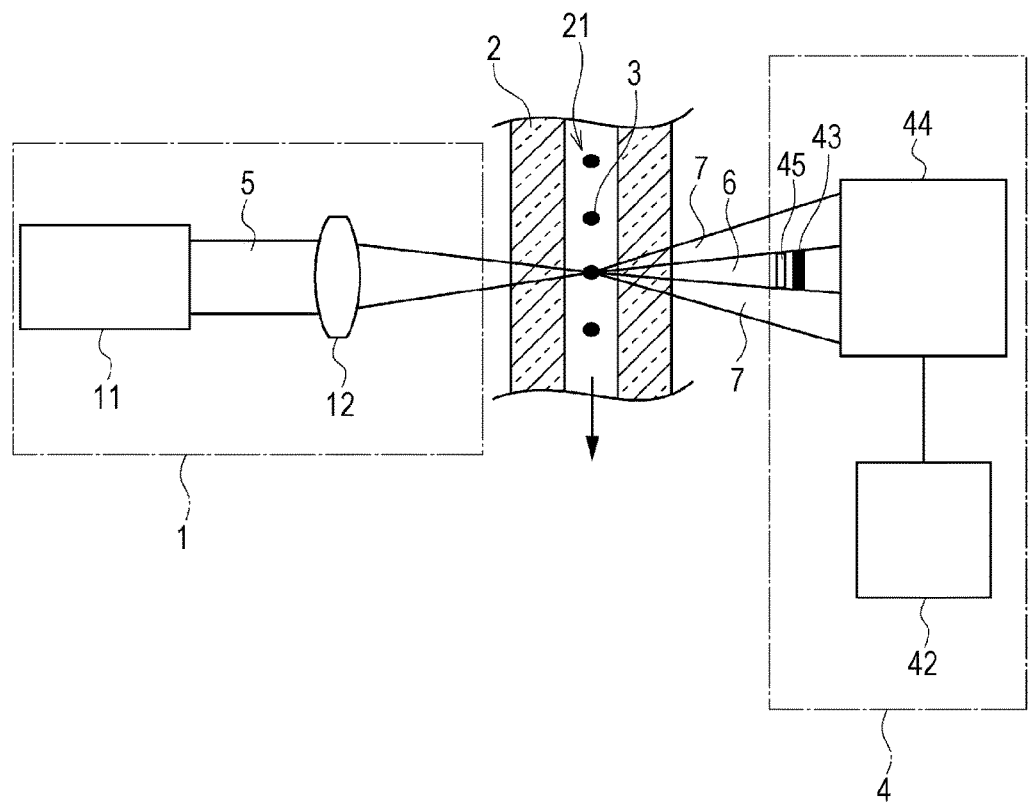
FIG. 9 is a diagram schematically illustrating a configuration of a particle detection apparatus in a first modification example of the second embodiment of the present disclosure.
Figure 10:
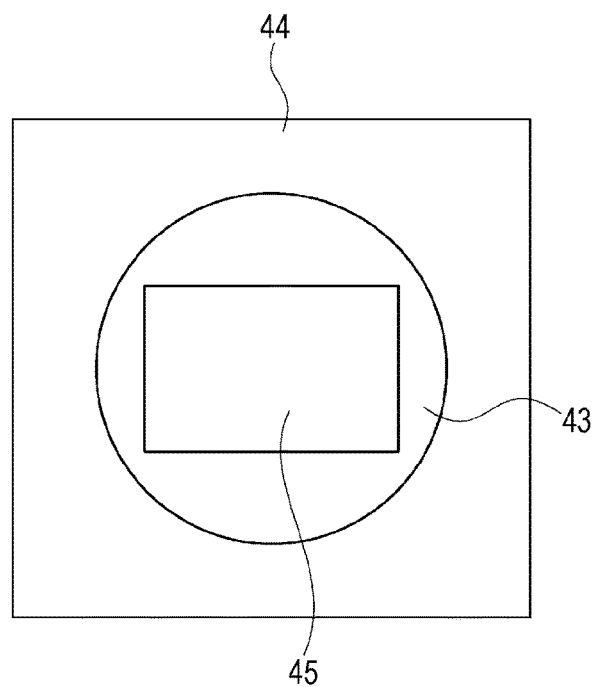
FIG. 10 is a diagram illustrating the positional relationship between the detection area of the scattered light detector 44, the zero-order light detector 45, and a zero-order light removing member 43 illustrated in FIG. 9.

Next, a particle detection apparatus according to a first modification example of the second embodiment of the present disclosure will be described. FIG. 9 is a diagram schematically illustrating a configuration of the particle detection apparatus in this modification example. FIG. 10 is a diagram illustrating the positional relationship between the detection area of the scattered light detector 44, the zero-order light detector 45, and a zero-order light removing member 43. In FIGS. 9 and 10, the same components as those of the particle detection apparatus in the above-described first embodiment and second embodiment are denoted by the same reference numerals, and will not be described in detail.

As illustrated in FIGS. 9 and 10, in the particle detection apparatus in this modification example, the zero-order light removing member 43 for intercepting the zero-order light 6 is disposed between the zero-order light detector 45 and the scattered light detector 44. By disposing the zero-order light removing member 43 in conjunction with the zero-order light detector 45, the noise removing effect can be further increased, and the accuracy of detecting scattered light can be improved. Components, operation, and effect other than those described above in this modification example are identical to those in the above-described first embodiment, modification example thereof, and second embodiment.

<5. Second Modification Example of Second Embodiment>

Figure 11:
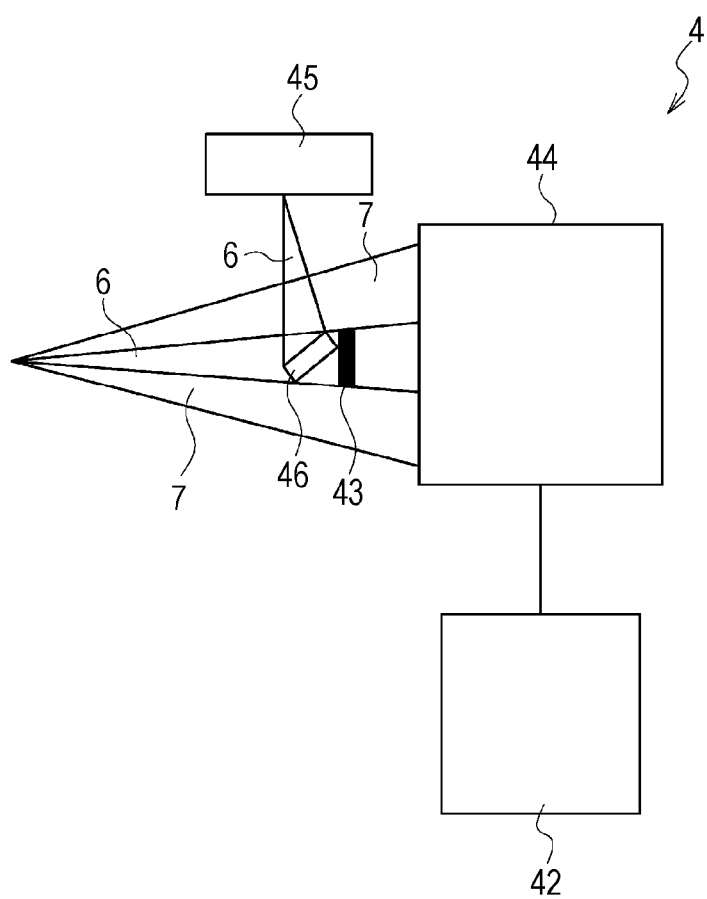
FIG. 11 is a diagram schematically illustrating a configuration of a scattered light detection unit 4 of a particle detection apparatus in a second modification example of the second embodiment of the present disclosure.

Although in the second embodiment illustrated in FIG. 7, the zero-order light detector 45 and the scattered light detector 44 are disposed on the optical path, the present disclosure is not limited to this, and the zero-order light detector 45 may alternatively be disposed outside the optical path. FIG. 11 is a diagram schematically illustrating a configuration of a scattered light detection unit 4 of the particle detection apparatus in this modification example.

As illustrated in FIG. 11, in the particle detection apparatus in this modification example, the zero-order light detector 45 is disposed outside the optical path, and a mirror 46 disposed on the optical path changes the optical path of the zero-order light 6 to guide the light to the zero-order light detector 45. In this case, in order to reduce the leaking of the zero-order light 6 thereinto, it is preferable to dispose the zero-order light removing member 43 between the mirror 46 and the scattered light detector 44.

Also in the particle detection apparatus in this modification example, the signal processing unit 42 removes a noise component from a signal detected by the scattered light detector 44, based on a signal detected by the zero-order light detector 45. Thus, forward scattered light can be detected with high accuracy as in the above-described modification example.

The present disclosure can take the following configuration.

(1)

A particle detection apparatus including:

a light illumination unit for illuminating a particle with light; and a scattered light detection unit for detecting scattered light emitted from the particle illuminated with light, the scattered light detection unit including:

a first detection portion for detecting the scattered light;

a second detection portion for detecting alight component originating in the illumination light onto the particle; and a signal processing unit for removing a noise component from a signal detected in the first detection portion based on a signal detected in the second detection portion.

(2)

The particle detection apparatus according to (1), wherein the first detection portion and the second detection portion are provided in a single light detector.

(3)

The particle detection apparatus according to (2), wherein the first detection portion is provided around the second detection portion.

(4)

The particle detection apparatus according to (2) or (3), wherein the light detector has a light-receiving surface divided into nine or more areas.

(5)

The particle detection apparatus according to any of (2) to (4), further including an illumination light removing member disposed in front of the light detector, the illumination light removing member intercepting the light component originating in the illumination light.

(6)

The particle detection apparatus according to (1), further including a scattered light detector functioning as the first detection portion, and an illumination light detector functioning as the second detection portion.

(7)

The particle detection apparatus according to (6), wherein the illumination light detector and the scattered light detector are disposed in this order on the optical path of the scattered light.

(8)

The particle detection apparatus according to (6) or (7), further including an illumination light removing member disposed between the illumination light detector and the scattered light detector, the illumination light removing member intercepting the light component originating in the illumination light.

(9)

The particle detection apparatus according to (6), further including a mirror for changing the optical path of the light component originating in the illumination light, wherein the illumination light detector is disposed outside the optical path of the scattered light.

(10)

The particle detection apparatus according to (9), further including an illumination light removing member disposed between the mirror and the scattered light detector, the illumination light removing member intercepting the light component originating in the illumination light.

(11)

The particle detection apparatus according to any of (1) to (10), wherein the signal processing unit removes the noise component by subtracting a detection signal of the second detection portion multiplied by a gain value from a detection signal of the first detection portion.

(12)

The particle detection apparatus according to any of (1) to (11), wherein the scattered light is forward scattered light.

(13)

The particle detection apparatus according to any of (1) to (12), wherein the light illumination unit illuminates a particle flowing through a flow path with light.

(14)

The particle detection apparatus according to (13), wherein the flow path is formed in a microchip.

(15)

A particle detection method including:

a light illumination step of illuminating a particle with light;

a scattered light detection step of detecting scattered light emitted from the particle in a first detection portion;

an illumination light step of detecting a light component originating in the illumination light onto the particle in a second detection portion; and a signal processing step of removing a noise component from a signal detected in the first detection portion based on a signal detected in the second detection portion.

(16)

The particle detection method according to (15), wherein in the signal processing step, the noise component is removed by subtracting the detection signal of the second detection portion multiplied by a gain value from the detection signal of the first detection portion.

(17)

The particle detection method according to (16), wherein the gain value is set based on the detection signal in the first detection portion and the detection signal in the second detection portion when light is emitted in the absence of the particle.

Reference Signs List

1 Light illumination unit
2 Microchip
3 Microparticle
4 Scattered light detection unit
5 Excitation light
6 Zero-order light
7 Scattered light
8 Light source
9 Lens
21 Flow path
41 Light detector
41*a* Scattered light detection area
41*b* Zero-order light detection area
42 Signal processing unit
43 Zero-order light removing member
44 Scattered light detector
45 Zero-order light detector
46 Mirror

The invention claimed is:

1. A particle detection apparatus, comprising:

a light illumination unit configured to illuminate a particle with light; and a scattered light detection unit configured to detect scattered light emitted from the particle illuminated with light, the scattered light detection unit including:
a first detection portion configured to detect the scattered light;
a second detection portion configured to detect a light component that originates in the illumination light onto the particle; and
a signal processing unit configured to remove a noise component from a signal detected in the first detection portion based on a signal detected in the second detection portion, wherein the noise component is removed based on a gain value, wherein said gain value is set based on a determination that light is emitted in an absence of the particle.

2. The particle detection apparatus according to claim 1, wherein the first detection portion is around the second detection portion.

3. The particle detection apparatus according to claim 1, further comprising a light detector that has a light-receiving surface divided into at least nine areas.

4. The particle detection apparatus according to claim 3, further comprising an illumination light removing member in front of the light detector, wherein the illumination light removing member is configured to intercept the light component that originates in the illumination light.

5. The particle detection apparatus according to claim 1, further comprising a scattered light detector that functions as the first detection portion, and an illumination light detector that functions as the second detection portion.

6. The particle detection apparatus according to claim 5, wherein the illumination light detector and the scattered light detector are arranged in this order on an optical path of the scattered light.

7. The particle detection apparatus according to claim 6, further comprising an illumination light removing member between the illumination light detector and the scattered light detector, wherein the illumination light removing member is configured to intercept the light component that originates in the illumination light.

8. The particle detection apparatus according to claim 5, further comprising a mirror configured to change an optical path of the light component that originates in the illumination light, wherein the illumination light detector is outside the optical path of the scattered light.

9. The particle detection apparatus according to claim 8, further comprising an illumination light removing member between the mirror and the scattered light detector, wherein the illumination light removing member is configured to intercept the light component that originates in the illumination light.

10. The particle detection apparatus according to claim 1, wherein the signal processing unit is further configured to remove the noise component based on subtraction of the detection signal of the second detection portion multiplied by the gain value from the detection signal of the first detection portion.

11. The particle detection apparatus according to claim 1, wherein the scattered light is forward scattered light.

12. The particle detection apparatus according to claim 1, wherein the light illumination unit is further configured to illuminate a particle that flows through a flow path with light.

13. The particle detection apparatus according to claim 12, wherein the flow path is formed in a microchip.

14. A particle detection method, comprising:
illuminating a particle with light;
detecting scattered light emitted from the particle in a first detection portion;
detecting a light component originating in the illumination light onto the particle in a second detection portion; and
removing a noise component from a signal detected in the first detection portion based on a signal detected in the second detection portion,
wherein the noise component is removed based on a gain value, wherein said gain value is set based on a determination that light is emitted in an absence of the particle.

15. The particle detection method according to claim 14, wherein the noise component is removed by subtracting the detection signal of the second detection portion multiplied by the gain value from the detection signal of the first detection portion.

16. The particle detection method according to claim 14, wherein the gain value is set based on the detection signal in the first detection portion and the detection signal in the second detection portion.

* * * * *